United States Patent
Chace et al.

(10) Patent No.: US 6,495,825 B1
(45) Date of Patent: Dec. 17, 2002

(54) APPARATUS FOR PHOTO EXPOSURE OF MATERIALS WITH SUBSEQUENT CAPTURING OF VOLATILES FOR ANALYSIS

(75) Inventors: Mark S. Chace, Beacon, NY (US); John E. Darney, Pine Bush, NY (US); David R. Medeiros, Ossining, NY (US); Wayne M. Moreau, Wappingers Falls, NY (US); Alfred O. Passano, Jr., Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/469,373

(22) Filed: Dec. 22, 1999

(51) Int. Cl.[7] .............................................. H01J 49/00
(52) U.S. Cl. ..................................................... 250/288
(58) Field of Search .................................. 250/287, 288

(56) References Cited

U.S. PATENT DOCUMENTS

| | | | |
|---|---|---|---|
| 4,914,297 A | * 4/1990 | Wieboldt et al. | 250/343 |
| 5,416,322 A | 5/1995 | Chace et al. | 250/288 |
| 5,526,110 A | * 6/1996 | Braymen | 250/252.1 |
| 5,528,032 A | 6/1996 | Uchiyama | 250/288 |
| 5,530,319 A | 6/1996 | Adam et al. | 315/106 |
| 5,742,050 A | * 4/1998 | Amirav et al. | 250/287 |
| 5,822,063 A | 10/1998 | Suzuki et al. | 356/364 |
| 5,876,904 A | 3/1999 | Uetani | 430/326 |
| 5,983,673 A | 11/1999 | Urano et al. | 65/30.1 |
| 6,084,237 A | * 7/2000 | Troster et al. | 250/288 |
| 6,144,029 A | * 11/2000 | Adler | 250/286 |
| 6,320,170 B1 | * 11/2001 | Jennings et al. | 219/679 |

* cited by examiner

*Primary Examiner*—John R. Lee
*Assistant Examiner*—Johnnie L Smith, II
(74) *Attorney, Agent, or Firm*—Steven Capella

(57) ABSTRACT

Real-time analysis of output volatiles upon UV exposure is achieved using a laboratory scale apparatus. The methods and apparatus use external or internal radiation sources, especially broad band external UV radiation. The apparatus and methods of the invention are especially useful in the analysis and screening of photoresist materials. The apparatus preferably uses FTIR or MS analysis.

19 Claims, 5 Drawing Sheets

Section A-A

Section B-B

Section C-C

APPARATUS FOR PHOTO EXPOSURE OF MATERIALS WITH SUBSEQUENT CAPTURING OF VOLATILES FOR ANALYSIS

BACKGROUND OF THE INVENTION

The analysis and prediction of the performance of materials upon exposure to radiation, such as ultraviolet radiation, is important for many industrial and commercial applications.

One industrial area where such analysis and prediction is especially important is in the area of photolithography. Photolithographic processes typically involve the use of organic photoresist materials which are patternwise exposed to radiation (most typically some form of ultraviolet radiation. Modern photoresist chemicals typically rely on radiation-induced chemical process that results in emission of volatiles. Such volatiles may cause catastrophic or incremental damage to expensive photolithographic equipment.

It may also be desired to determine the chemical effects of ultraviolet or other radiation exposure in order to obtain information regarding the actual chemical processes occurring in a multi-component chemical system such as a photoresist. Such information may be useful in determining the proper components and proportions to be used in the photoresist formulation.

Unfortunately, photoresist development typically takes place in an ordinary chemical laboratory where access to photolithographic equipment is not possible or impractical (e.g., due to logistics, expense, etc.) or is undesirable (e.g., where equipment damage is a concern). In the laboratory, it is difficult to simulate actual photochemical and catalytic processes that would occur upon radiation exposure in the photolithographic tool. A typical solution to this problem has been to use heating or action of chemical treatments to simulate the reactions that would occur in the photolithographic tool. These methods have not been adequate to reliably predict volatiles evolution.

Thus, there is a need for improved laboratory methods and laboratory scale apparatus for determining the performance of materials upon irradiation.

SUMMARY OF THE INVENTION

The invention provides a laboratory scale apparatus for simulation of UV radiation exposure behavior with real time analysis of output volatiles. The invention also provides methods of performing real time analysis of volatile species generated upon UV irradiation of a material sample. The apparatus and methods of the invention are especially useful in the analysis and screening of photoresist materials.

In one aspect, the invention encompasses an apparatus for analysis of volatiles emitted from a material sample upon exposure to radiation, the apparatus comprising:

a) a chamber adapted to hold a material sample, the chamber comprising (i) a window for transmission of radiation to the sample, (ii) a holder for the sample, (iii) an inlet for sweep gas, and (iv) an outlet for volatiles-containing sweep gas, b) a gas supply means for supplying sweep gas to the chamber, c) a radiation source for transmitting radiation to the sample through the window, and d) a volatiles analyzing means adapted to receive and analyze volatiles-containing gas passing from the chamber through the outlet upon exposure of the sample to radiation from the radiation source.

In another aspect, the invention encompasses a method of determining the composition of volatiles emitted from a material upon exposure to UV radiation, the method comprising:

a) placing the material on a substrate, b) placing the substrate in a chamber adapted to hold the substrate, the chamber comprising (i) a window for transmission of radiation to the substrate, (ii) an inlet for sweep gas, and (iv) an outlet for volatiles-containing sweep gas, c) supplying sweep gas to the chamber, d) irradiating the substrate by transmitting radiation through the window, thereby causing evolution of volatiles from the material, the volatiles being entrained in the sweep gas, e) analyzing the volatiles-containing sweep gas using spectroscopy, the analysis being conducted as the volatiles are being formed during the irradiation.

The apparatus and methods of the invention are especially useful for the analysis of photoresist materials. A preferred analysis is mass spectroscopy or Fourier Transform Infrared Spectroscopy (FTIR). The irradiation is preferably performed with an ultraviolet radiation source capable of producing radiation at wavelengths of about 400 nm or less.

These and other aspects of the invention are described in further detail below.

DETAILED DESCRIPTION OF THE INVENTION

The invention provides a laboratory scale apparatus for simulation of UV radiation exposure behavior with real time analysis of output volatiles. The invention also provides methods of performing real time analysis of volatile species generated upon UV irradiation of a material sample. The apparatus and methods of the invention are especially useful in the analysis and screening of photoresist materials.

Figure 1:
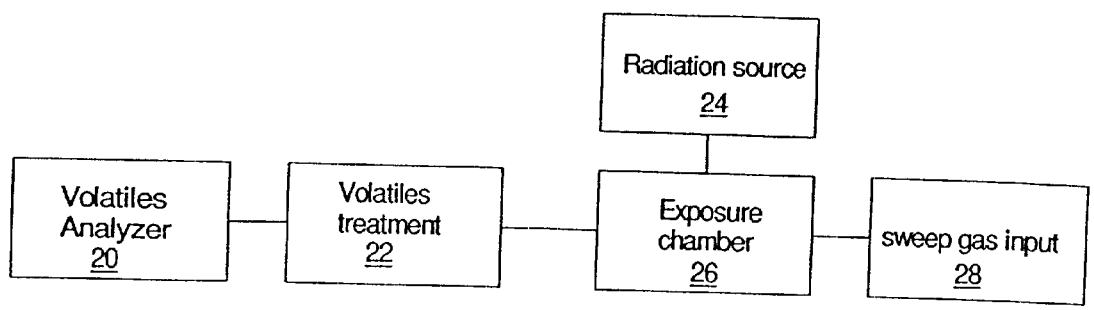
FIG. 1 is a block diagram of an embodiment of the apparatus of the invention.

An embodiment of the apparatus of the invention is illustrated schematically in FIG. 1. The apparatus 10 generally comprises an exposure chamber 26 which houses a sample holder 30 (FIG. 2). Exposure chamber 26 is in communication with a source of sweep gas 28 which may be input to chamber 26. The apparatus further includes a radiation source 24 which is capable of directing radiation to a sample 32 in sample holder 30. Chamber 26 (and/or sample holder 30) are designed with a window 34 to permit access to the sample 32 by radiation source 24 as is discussed further below. Exposure chamber 26 is also in communication with a volatiles analyzer 20 for receiving volatiles carried from chamber 26 by sweep gas. The apparatus may optionally include additional components between exposure chamber 26 and analyzer 20 such as a treatment stage 22 which may include means such as diluting means, heating means, cooling means, etc. which may be desirable to facilitate analysis of the sample in analyzer 20.

Figure 2A:
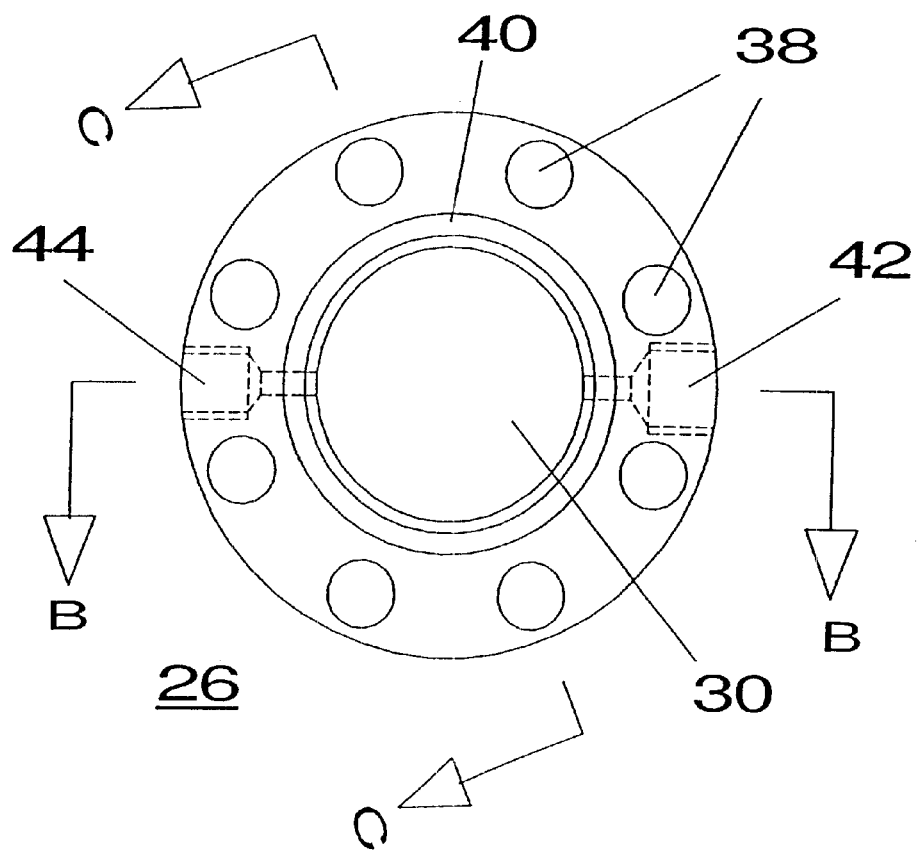
FIG. 2A is a plan view cross-section schematic illustration of an embodiment sample holder and exposure chamber useful in the apparatus of the invention taken at cut A—A in FIGS. 2B and 2C with the projection of gas inlet and outlets shown.
Figure 2B:
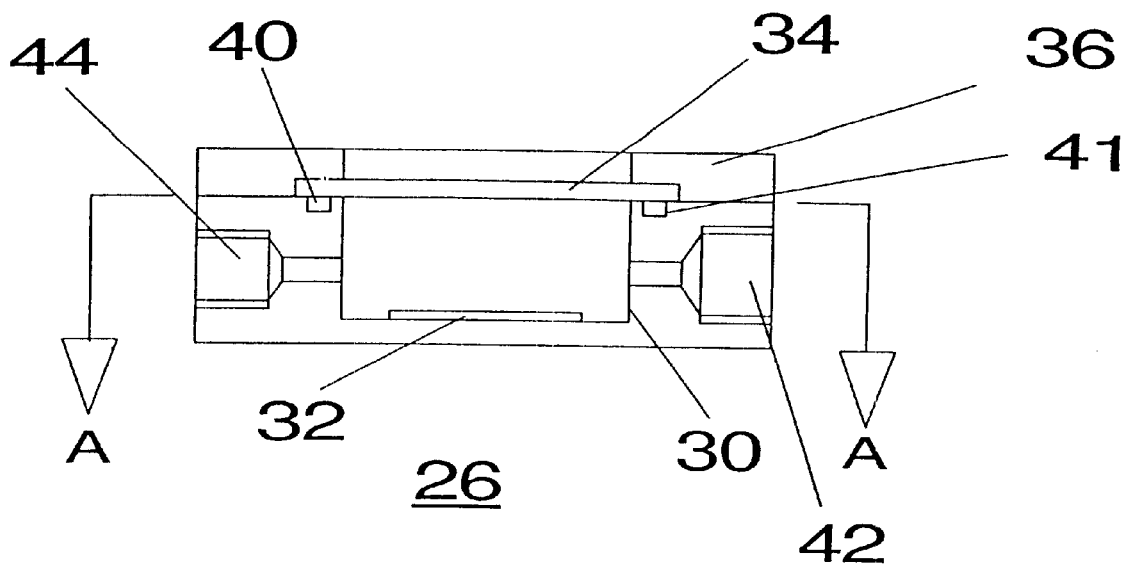
FIG. 2B is a cross-section schematic illustration of the sample holder and exposure chamber of FIG. 2A at cut B—B in FIG. 2A.
Figure 2C:
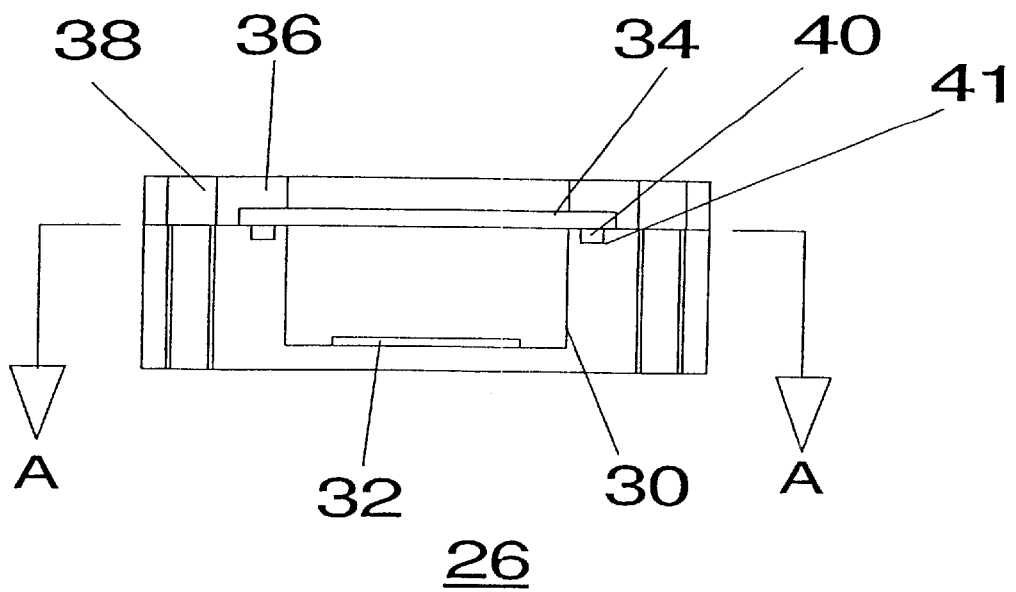
FIG. 2C is a cross-section schematic illustration of the sample holder and exposure chamber of FIG. 2A at cut C—C in FIG. 2A.

Referring to FIGS. 2A–C, the apparatus of the invention is preferably characterized by the use of a window 34 which is sufficiently transparent to the desired exposure radiation while also acting in combination with the other components of the sample holder 32 and chamber 26 to permit control of the atmosphere in which the sample is maintained during testing. Window 34 is preferably part of a separate cover 36 which is removably and sealably attached to the chamber 26. For example, cover 36 may be fixed to the chamber 24 by bolts 38 (in FIGS. 2A–C), screws, clamps or other fixing means. Preferably, chamber 24 includes a sealing expedient such as an o-ring 40 residing in annular groove 41 or other sealing means. Alternatively, the sample holder 32 may also be integral with cover 36 whereby the sample holder 32 and cover 36 may be removed or fixed in housing 26 at the same time.

Chamber 26 and sample holder 32 may be made of any suitable material. Generally, metallic materials such as aluminum, steel, alloys, etc. are preferred. Window 34 may be made of any suitable material having the necessary physical integrity and radiation transparency. For ultraviolet radiation in the wavelength range of 200–400 nm, a quartz window is preferred. It may be possible to use quartz down to about 180 nm, fluoride-treated quartz or other treated silicas may have suitable transmission for use with wavelengths on the order of 150–200 nm (e.g., the silica materials described in U.S. Pat. No. 5,983,673, the disclosure of which is incorporated herein by reference). Where the radiation wavelength is shorter (e.g., 100–200 nm), a material such as calcium fluoride ($CaF_2$) may be used as a window material.

Chamber 26 preferably further includes an inlet 42 for sweep gas from gas source 28. Inlet 42 may be connected to gas source 28 using any conventional means for conveying the gas without excessive leakage to or from the ambient atmosphere. For example, suitable tubing (not shown) may be coupled to inlet 42 and gas source 28. Preferably, any tubing used does not introduce excessive contaminants to the chamber, such as would hinder analysis of volatiles from the sample under test.

Chamber 26 also includes an outlet 44 for gas from chamber 26 to exit the chamber (e.g., for analysis, etc.) Outlet 44 is connected to analyzer 20 using any conventional means for conveying gas without excessive leakage to or from the ambient atmosphere.

Chamber 26 may also include other expedients such as cooling or heating means, temperature/pressure monitoring devices, etc.

If desired, a gas treatment means 22 may be incorporated in the path from outlet 44 to analyzer 20 using conventional connection means. Examples of possible treatment means include dilution chambers, heating elements, cooling elements, etc. See for example, the gas treatment means described in U.S. Pat. No. 5,416,322, the disclosure of which is incorporated herein by reference.

The sweep gas source 28 may be any suitable gas source. Typically, a comparatively inert gas such as nitrogen, argon, or helium is preferred. If desired, a pump, valve, regulator, and/or other flow controlling means may be used to control the flow rate of the sweep gas.

The radiation source 24 may be any suitable radiation source which can be provided on a laboratory scale. For deep UV and i-line radiation (e.g., 248–365 nm wavelengths), the radiation source is preferably broad band sources such as a mercury discharge lamp, used in conjunction with an appropriate bandpass filter. For shorter UV (e.g., 150–200 nm wavelengths), the radiation source is preferably a hydrogen discharge lamp or deuterium discharge lamp, used in conjunction with an appropriate bandpass filter. Alternatively, laser radiation sources such as excimer gas laser (e.g., using $F_2$, ArF, KrCl, KrF, or XeCl) or solid state laser may be used as appropriate.

Figure 3:
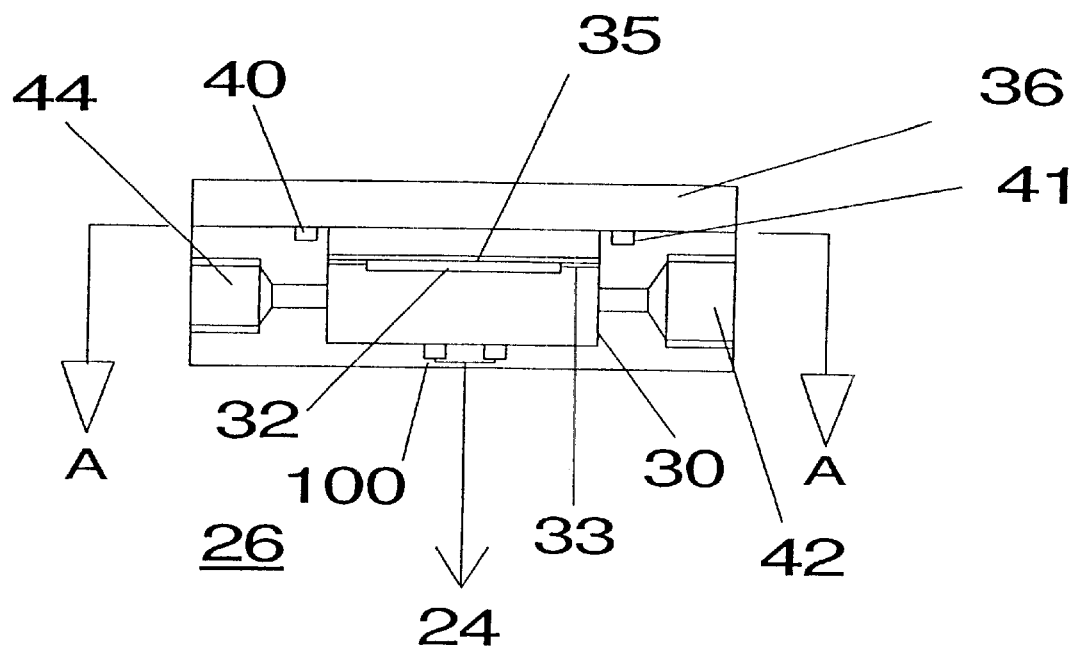
FIG. 3 is a schematic cross-section view of an embodiment sample holder and exposure chamber with internal transmission of radiation useful in the apparatus of the invention.

In an alternative embodiment of the invention (FIG. 3), an internal radiation source such as provided through a transmission means 100 such as fiber optic means may be incorporated into chamber 26. In such an embodiment, the use of transmission window 34 in cover 36 may be eliminated. A sample 32 on substrate 35 is held upside down by an annular rim 33. The radiation source 24 is transmitted from below through means 100.

The volatiles analyzing means may be any known suitable analyzing means. Preferably, the analyzing means is a device capable of performing a spectroscopic analytical technique. For example, Fourier Transform Infrared Spectroscopy (FTIR) or mass spectroscopy (MS) (e.g., such as Fourier Transform Mass Spec (FTMS), Time of Flight Mass Spec (TOF-MS), and Quadrupole MS). GC-MS (Gas Chromatography-Mass Spectroscopy) or other analytical techniques may also be used.

While not shown in the figures, it should be understood that the apparatus of the invention may include ancillary computer, microprocessor or other electronic control or monitoring devices connected to one or more of the above components to facilitate operation of the apparatus.

The invention encompasses methods of analyzing the composition of volatiles emitted from a material upon exposure to UV radiation. The methods of the invention preferably comprise:

a) placing the material on a substrate, b) placing the substrate in a chamber adapted to hold the substrate, the chamber comprising (i) a window for transmission of radiation to the substrate, (ii) an inlet for sweep gas, and (iv) an outlet for volatiles-containing sweep gas, c) supplying sweep gas to the chamber, d) irradiating the substrate by transmitting radiation through the window, thereby causing evolution of volatiles from the material, the volatiles being entrained in the sweep gas, e) analyzing the volatiles-containing sweep gas, the analysis being conducted as the volatiles are being formed during the irradiation.

The material to be analyzed is preferably a photoresist material which may be placed on the substrate using any conventional technique such as spin-coating or other technique where the substrate is preferably a wafer or wafer-like article. Alternatively, where the material to be tested has sufficient mechanical integrity, step a) may simply comprise providing a solid sample of the material (i.e., the use of a separate substrate may be eliminated in such instance.) Where the material sample is coated onto the substrate, preferably any solvent present in the sample is removed by drying, pre-exposure baking or out-gassing of the sample before radiation exposure.

The apparatus provided in step b) is preferably the apparatus of the invention described above.

The flow of sweep gas in step c) may be conducted using any desired sweep gas, preferably a relatively inert gas such as nitrogen, argon, helium or a combination thereof. The sweep gas pressure, flow rate any temperature may be selected as desired to facilitate the analysis of the volatiles emitted from the sample. Preferably, the sweep gas is supplied at ambient temperature and pressure. If desired, the sweep gas flow may be initiated for some time prior to irradiation to facilitate removal of solvent volatiles from the sample. The analyzer or other monitoring device may be activated during such removal to monitor the level of solvent volatiles. The apparatus and methods of the invention techniques can detect solvents and therefore are useful to identify residual casting solvents.

The radiation exposure may be conducted using any suitable radiation source such as those discussed above in connection with the apparatus of the invention. The radiation exposure is preferably selected to provide an exposure energy dose of analytical interest, for example an energy dose typical of a photolithographic process. If desired, the radiation exposure may be conducted without flow of sweep gas or with intermittent flow of sweep gas depending on the analytical technique as long as the volatiles are ultimately suitably removed from the chamber for analysis. If desired, the sample may be heated or cooled during radiation exposure. Also, radiation exposure may be performed at ambient, elevated or reduced pressure as desired. Preferably, exposure is performed at ambient pressure and temperature.

If the alternative apparatus of the invention is used, then steps b) and d) would be modified in that a window would not be required in step b) and irradiation in step d) would not involve transmission through a window.

The volatiles-containing sweep gas may be analyzed using any suitable technique. Preferably, the analyzing technique is preferably a spectroscopic analytical technique. For example, Fourier Transform Infrared Spectroscopy (FTIR) or mass spectroscopy (MS) (e.g., such as Fourier Transform Mass Spec (FTMS), Time of Flight Mass Spec (TOF-MS), and Quadrupole MS). GC-MS (Gas Chromatography-Mass Spectroscopy) or other analytical techniques may also be used.

If desired, the volatiles-containing sweep gas may be treated prior to analysis. For example, the gas may be heated, cooled, diluted, etc. If desired, a portion of the volatiles-containing sweep gas may be divided out for analysis by a second analyzing means.

The methods of the invention may include use of devices such as computers, microprocessor or other electronic control or monitoring devices to facilitate the process of the invention.

What is claimed is:

1. An apparatus for analysis volatiles emitted from a material sample upon exposure to radiation, said apparatus comprising:
    a) a chamber adapted to hold a material sample, said chamber comprising (i) a window for transmission of radiation to the sample, (ii) a holder for said sample, (iii) an inlet for sweep gas, and (iv) an outlet for volatiles-containing sweep gas,
    b) a gas supply means for supplying sweep gas to said chamber,
    c) a radiation source for transmitting radiation to said sample through said window, said radiation source being a discharge lamp, and
    d) a volatiles analysis means adapted to receive and analyze volatiles-containing gas passing from said chamber through said outlet upon exposure of said sample to radiation from said radiation source.

2. The apparatus of claim 1 wherein said window comprises a glass material.

3. The apparatus of claim 1 wherein said chamber is air-tight except for said inlet and outlet.

4. The apparatus of claim 1 wherein said analyzing means is a spectroscopy device.

5. The apparatus of claim 1 further comprising a dilution chamber between said outlet and said analyzing means, said dilution chamber being in communication with said outlet and said analyzing means whereby said volatiles-containing gas passes from said outlet through said dilution chamber to said analyzing means.

6. The apparatus of claim 5 further comprising a dilution gas source adapted to be mixed with said volatiles-containing gas in said dilution chamber.

7. The apparatus of claim 1 wherein said radiation source is selected from the group consisting of a mercury discharge lamp, a hydrogen discharge lamp, and a deuterium discharge lamp.

8. The apparatus of claim 1 further comprising a housing, containing said chamber.

9. The apparatus of claim 8 comprising means for releasably fixing said chamber in said housing.

10. The apparatus of claim 4 wherein said spectroscopy device is capable of performing an analytical technique selected from the group consisting of FTIR and mass spectroscopy.

11. A method of analyzing volatiles emitted from a photoresist material upon exposure to radiation, said method comprising:
    a) placing the photoresist material on a substrate,
    b) placing said substrate in a chamber adapted to hold said substrate, said camber comprising (i) a window for transmission of radiation to the substrate, (ii) an inlet for sweep gas, and (iv) an outlet for volatiles-containing sweep gas,
    c) supplying sweep gas to said chamber,
    d) irradiating said substrate by transmitting radiation from a discharge lamp through said window, thereby causing evolution of volatiles from said sample material, said volatiles being entrained in said sweep gas,
    e) analyzing said volatiles-containing sweep gas, said analysis being conducted as said volatiles are being formed during said irradiation.

12. The method of claim 11 further comprising diluting said volatiles-containing sweep gas prior to the analysis of step e).

13. The method of claim 11 wherein said irradiation comprises directing a radiation source through said window, said radiation source being selected from the group consisting of a mercury discharge lamp, a hydrogen discharge lamp, and a deuterium discharge lamp.

14. The method of claim 11 wherein analyzing comprises a spectroscopy technique selected from the group consisting of FTIR and mass spectroscopy.

15. The method of claim 11 wherein said irradiation is conducted at atmospheric pressure.

16. The method of claim 11 wherein said irradiation is conducted in the absence of heat input.

17. The method of claim 11 wherein said material is a photoresist material selected from the group consisting of I-line photoresist, deep UV photoresist, 193 nm photoresist and 157 nm photoresist.

18. An apparatus for analysis volatiles emitted from a material sample upon exposure to radiation, said apparatus comprising:
    a) a chamber adapted to hold a material sample, said chamber comprising (i) an internal discharge lamp radiation source, (ii) a holder for said sample, (iii) an inlet for sweep gas, and (iv) an outlet for volatiles-containing sweep gas, b) a gas supply means for supplying sweep gas to said chamber, and c) a volatiles analysis means adapted to receive and analyze volatiles-containing gas passing from said chamber through said outlet upon exposure of said sample to radiation from said radiation source.

19. The method of claim 11 wherein said radiation causes a radiation-induced chemical process resulting in such volatiles emission.